(12) United States Patent
Philippon et al.

(10) Patent No.: US 9,931,150 B2
(45) Date of Patent: Apr. 3, 2018

(54) ANCHOR DELIVERY SYSTEM

(71) Applicant: Smith & Nephew, Inc., Memphis, TN (US)

(72) Inventors: Marc Joseph Philippon, Edwards, CO (US); Kevin Murphy, Ponte Vedra Beach, FL (US); Rebecca A. Blough, West Warwick, RI (US); Paul Alexander Torrie, Marblehead, MA (US); Paul A. Puniello, Bristol, RI (US); Paul S. Vincuilla, Bellingham, MA (US); Paul McCabe, Mansfield, MA (US); Gary R. Vario, Warwick, RI (US); Michael C. Ferragamo, Foster, RI (US); Justin Dye, Mansfield, MA (US); John M. Lipchitz, Watertown, MA (US)

(73) Assignee: Smith & Nephew, Inc., Memphis, TN (US)

( * ) Notice: Subject to any disclaimer, the term of this patent is extended or adjusted under 35 U.S.C. 154(b) by 0 days.

(21) Appl. No.: 15/429,477

(22) Filed: Feb. 10, 2017

(65) Prior Publication Data

US 2017/0151007 A1 Jun. 1, 2017

Related U.S. Application Data

(62) Division of application No. 14/274,977, filed on May 12, 2014, now Pat. No. 9,572,564, which is a division of application No. 11/839,721, filed on Aug. 16, 2007, now Pat. No. 8,758,367.

(60) Provisional application No. 60/824,573, filed on Sep. 5, 2006.

(51) Int. Cl.
*A61B 17/60* (2006.01)
*A61B 17/88* (2006.01)
*A61B 17/04* (2006.01)

(52) U.S. Cl.
CPC ...... *A61B 17/8888* (2013.01); *A61B 17/0401* (2013.01); *A61B 2017/0409* (2013.01); *A61B 2017/0411* (2013.01)

(58) Field of Classification Search
USPC ................................ 606/139–145, 148, 232
See application file for complete search history.

(56) References Cited

U.S. PATENT DOCUMENTS

| | | | | |
|---|---|---|---|---|
| 5,139,520 | A * | 8/1992 | Rosenberg | A61B 17/1675 606/102 |
| 5,258,016 | A * | 11/1993 | DiPoto | A61B 17/0401 606/104 |
| 5,827,291 | A * | 10/1998 | Fucci | A61B 17/0401 606/104 |
| 5,868,789 | A * | 2/1999 | Huebner | A61B 17/0401 606/232 |
| 5,944,739 | A * | 8/1999 | Zlock | A61B 17/0401 206/339 |

(Continued)

*Primary Examiner* — Matthew Lawson
(74) *Attorney, Agent, or Firm* — Norman F. Hainer, Jr.

(57) ABSTRACT

An anchor delivery tool is described. The tool includes a shaft and a handle coupled to a proximal portion of the shaft. The handle includes a hub, with a knob and a nose cone coupled to the hub. The knob and nose cone may be spring loaded so as to selectively retain a length of suture disposed therebetween. The tool further includes an anchor, such as a suture anchor, coupled to a distal portion of the shaft.

19 Claims, 12 Drawing Sheets

FIG. 9A

(56) References Cited

U.S. PATENT DOCUMENTS

| | | | | |
|---|---|---|---|---|
| 5,993,459 A | * | 11/1999 | Larsen | A61B 17/0469 606/104 |
| 2002/0188301 A1 | * | 12/2002 | Dallara | A61B 17/064 606/104 |
| 2002/0193807 A1 | * | 12/2002 | Chen | A61B 17/068 606/129 |
| 2005/0070918 A1 | * | 3/2005 | Zwirnmann | A61B 17/068 606/916 |
| 2005/0240199 A1 | * | 10/2005 | Martinek | A61B 17/0401 606/104 |

* cited by examiner

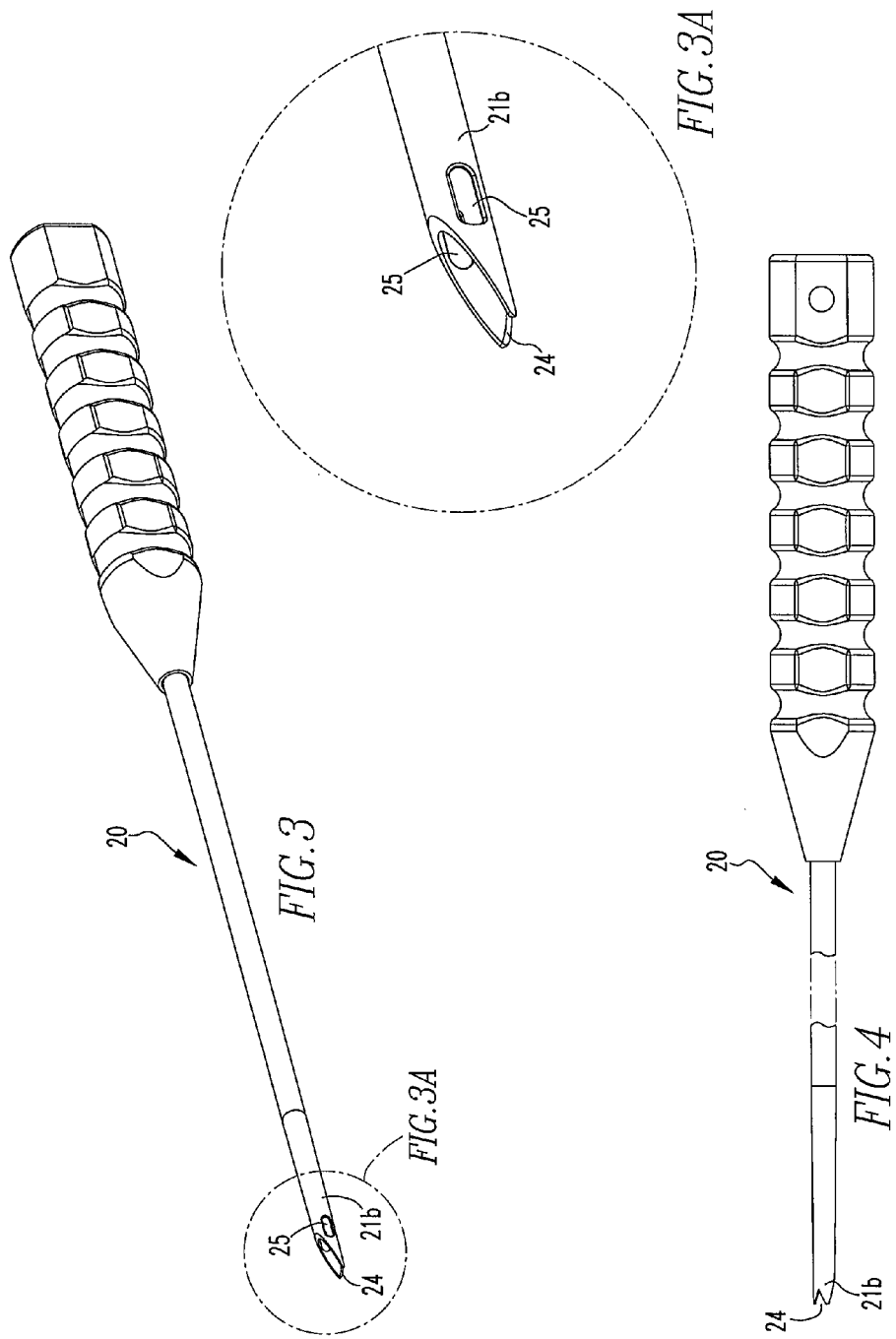

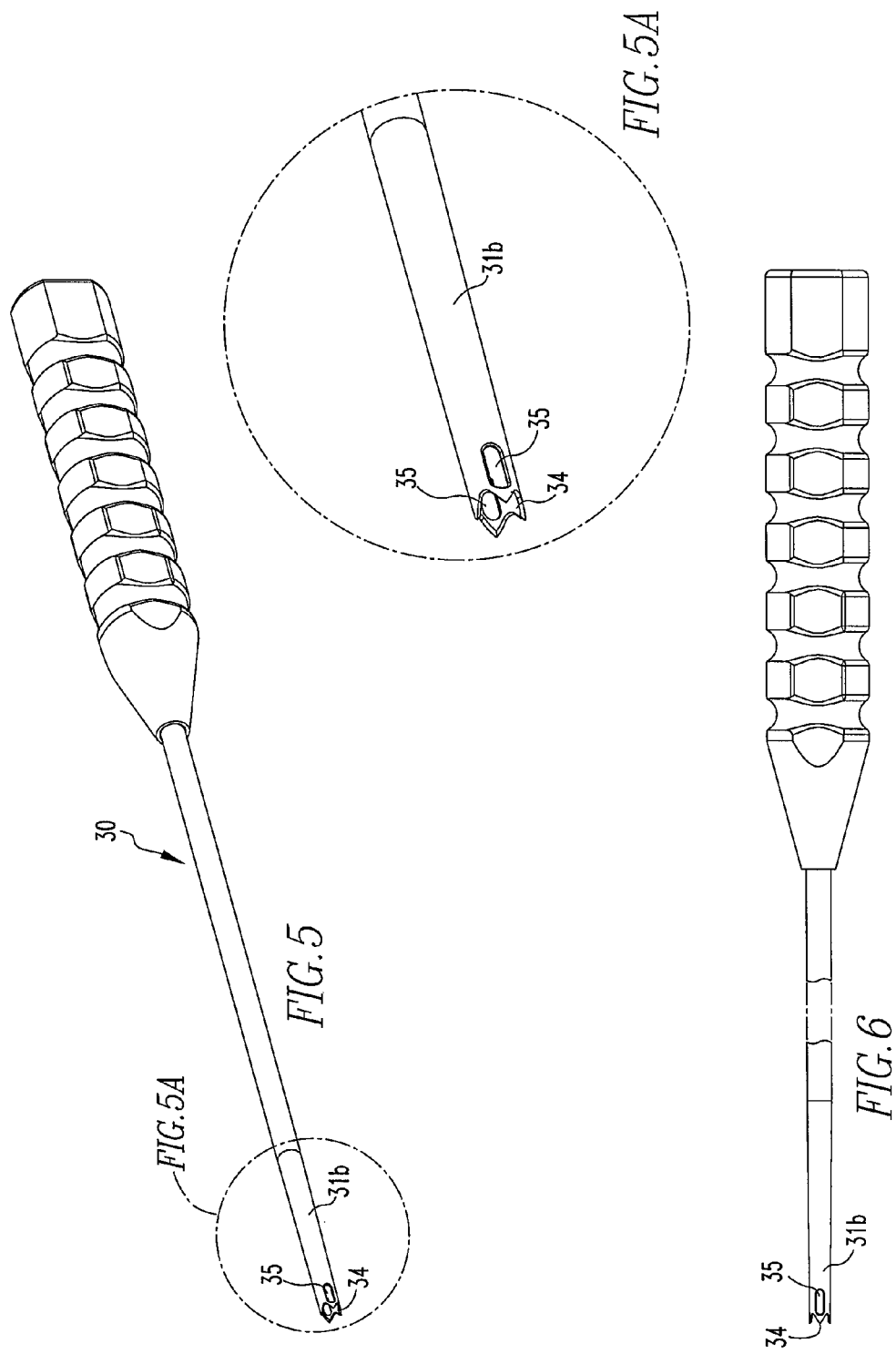

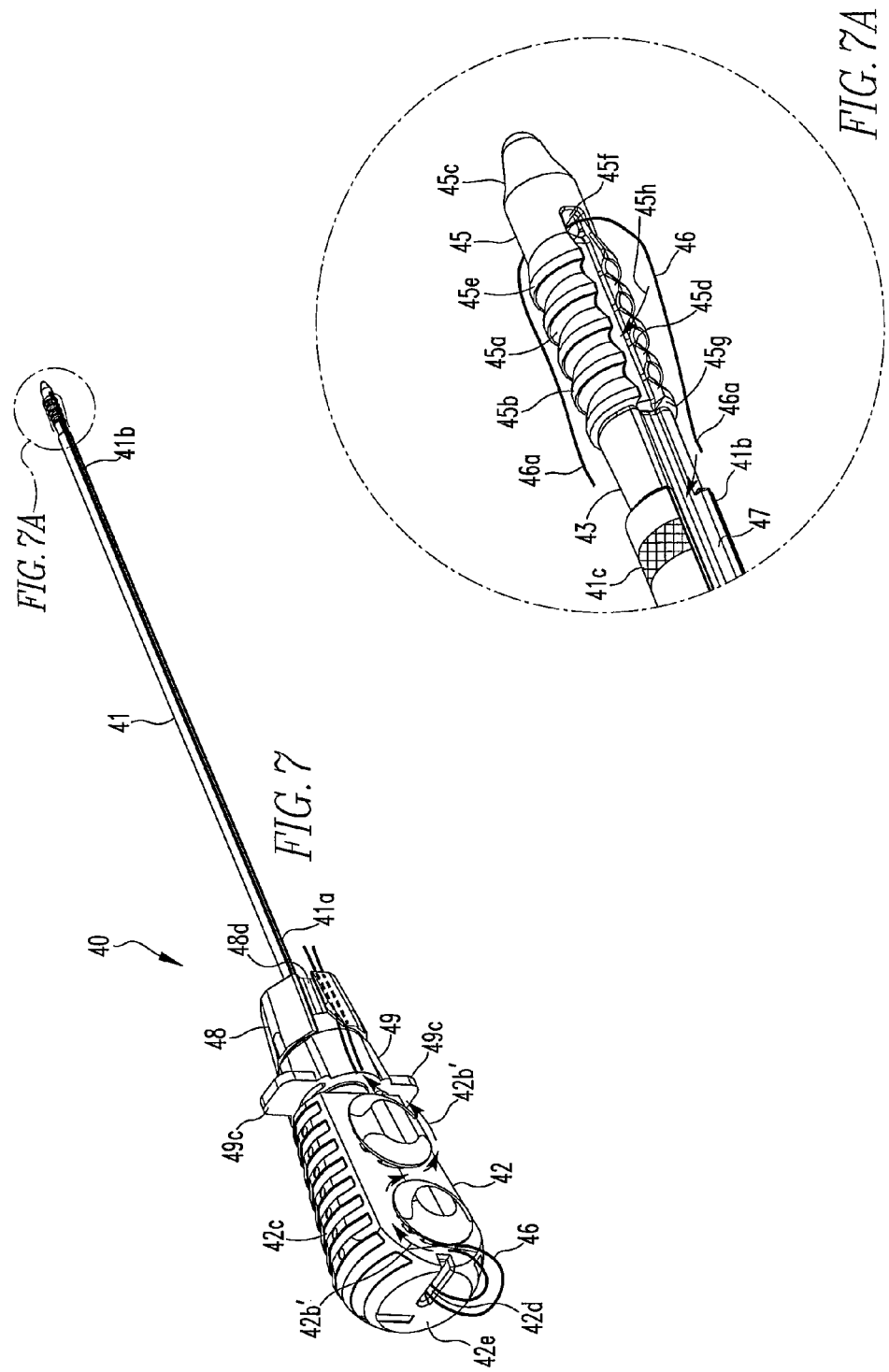

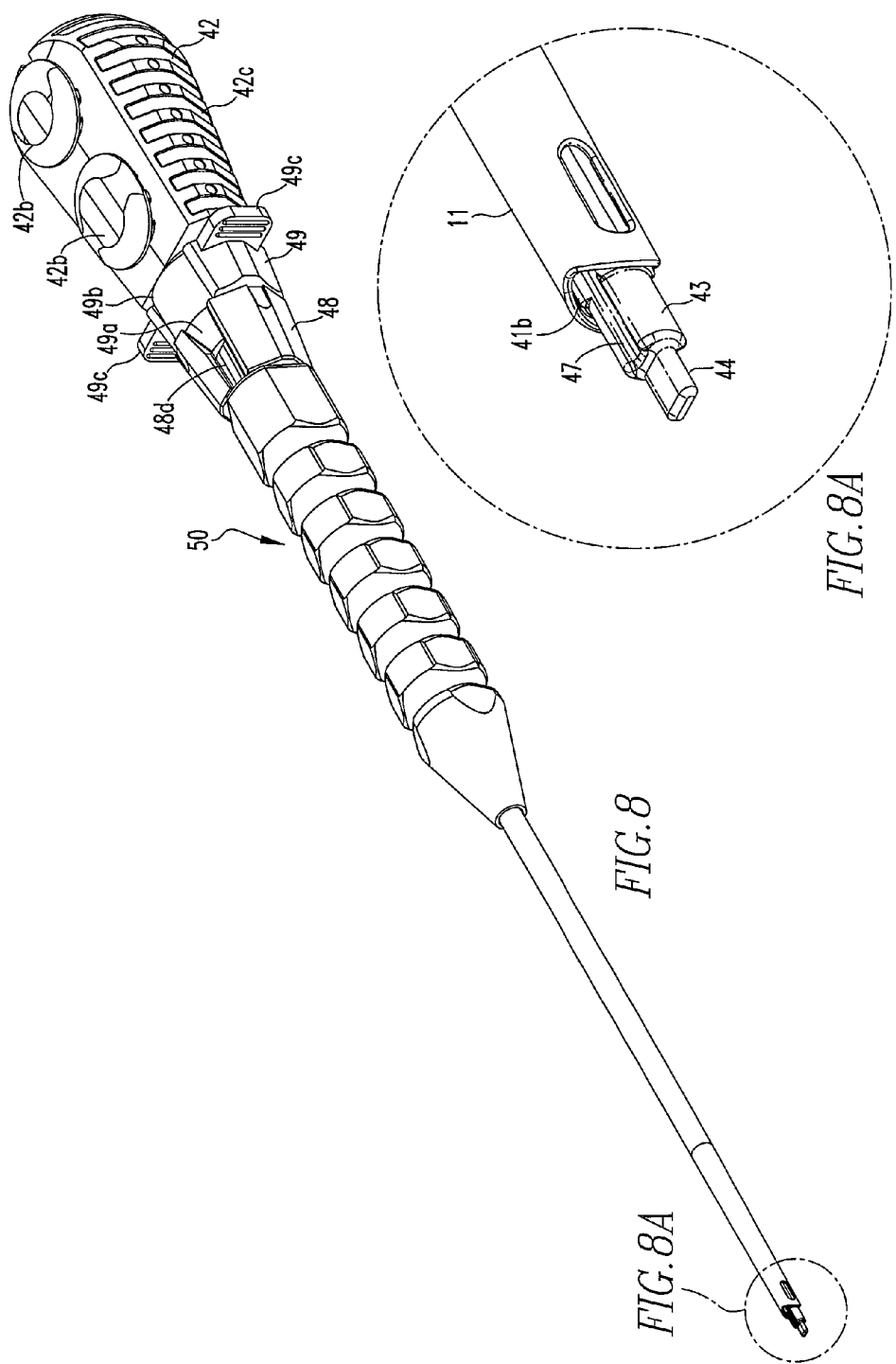

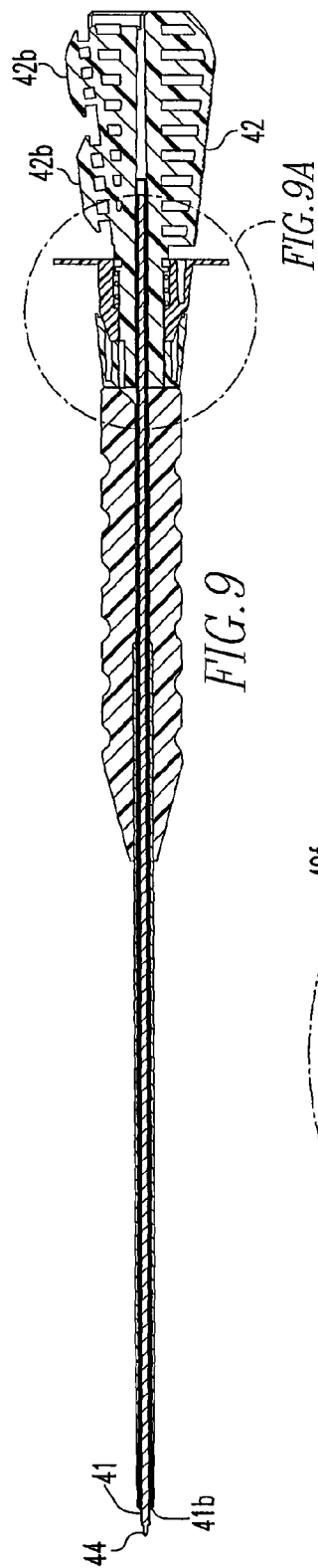
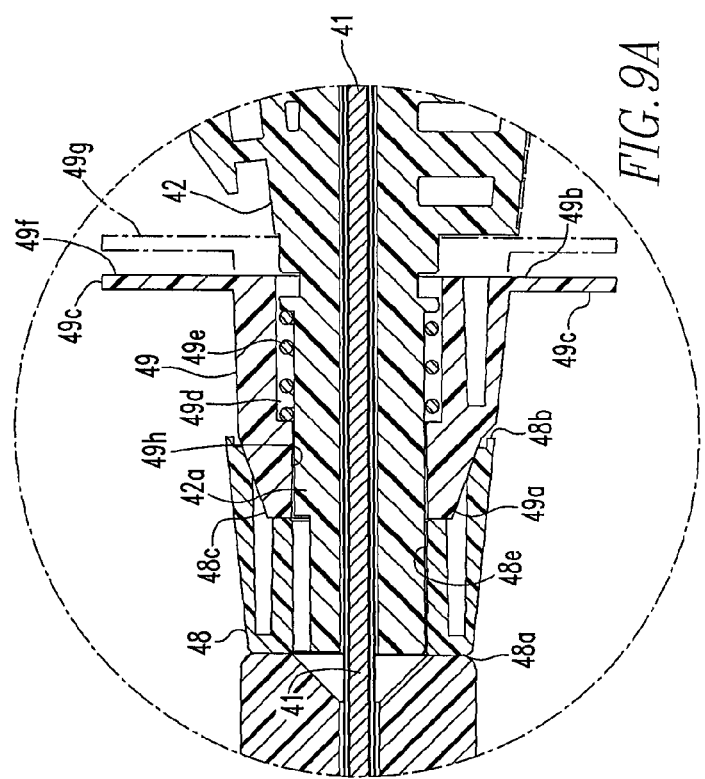

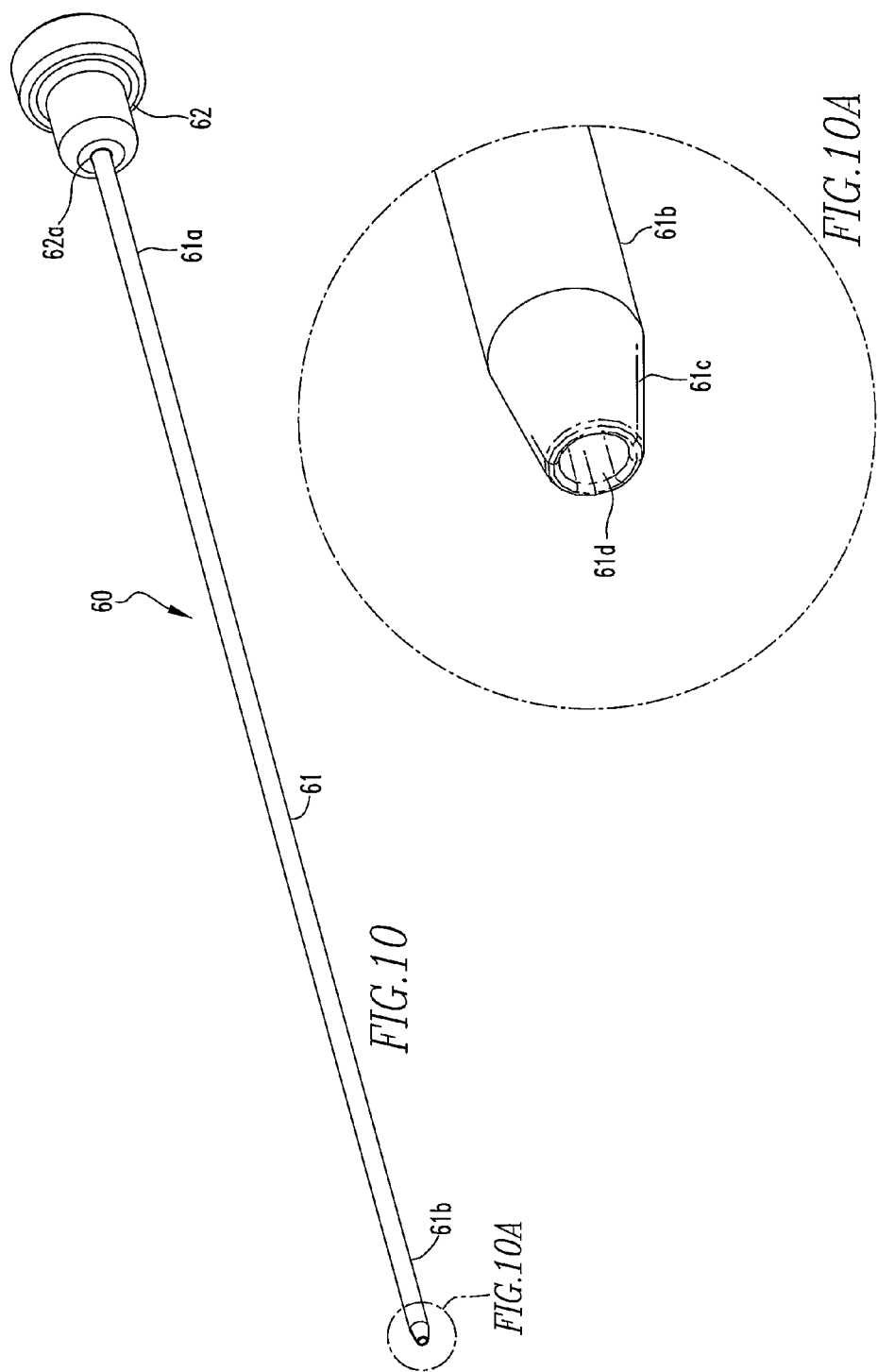

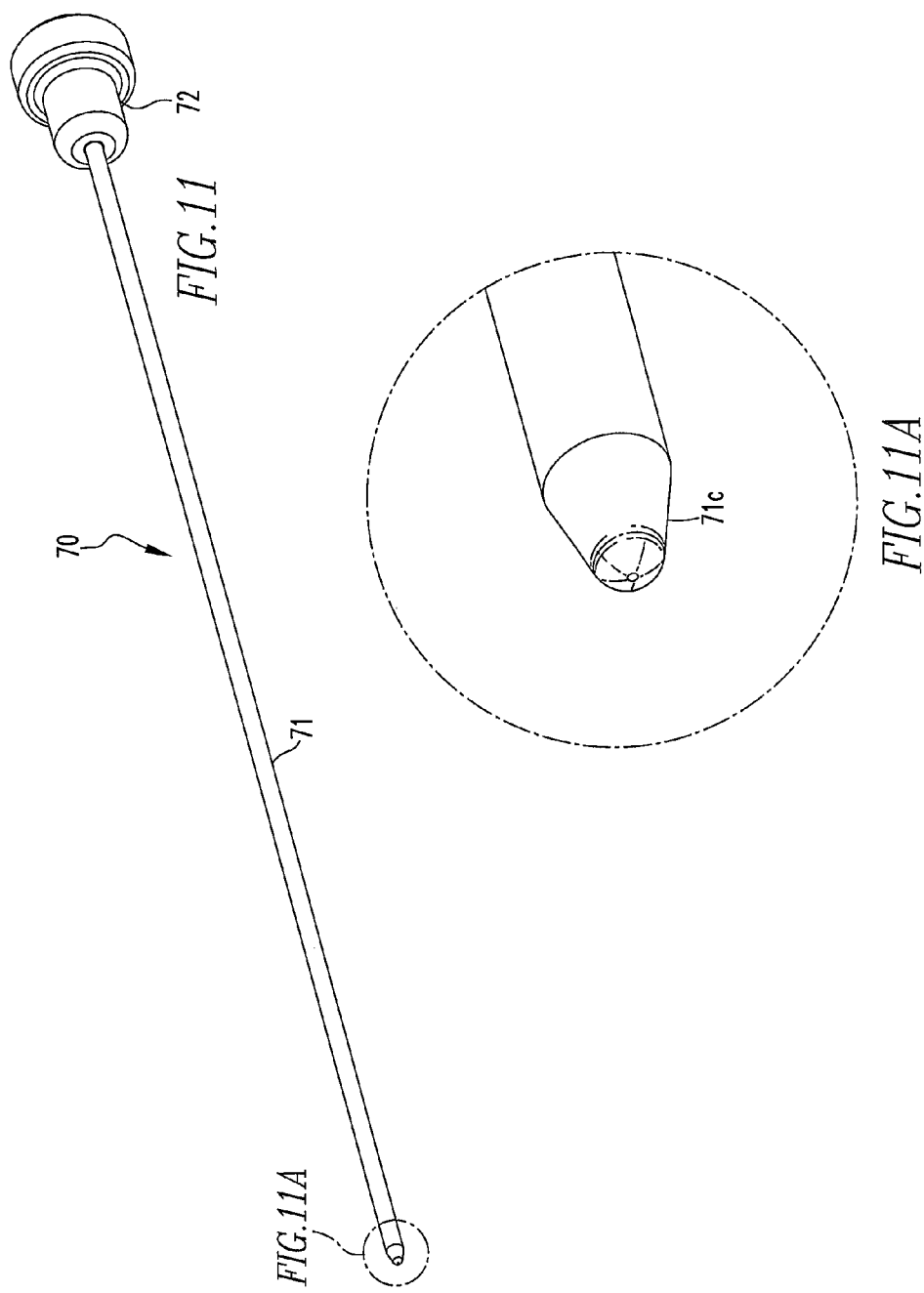

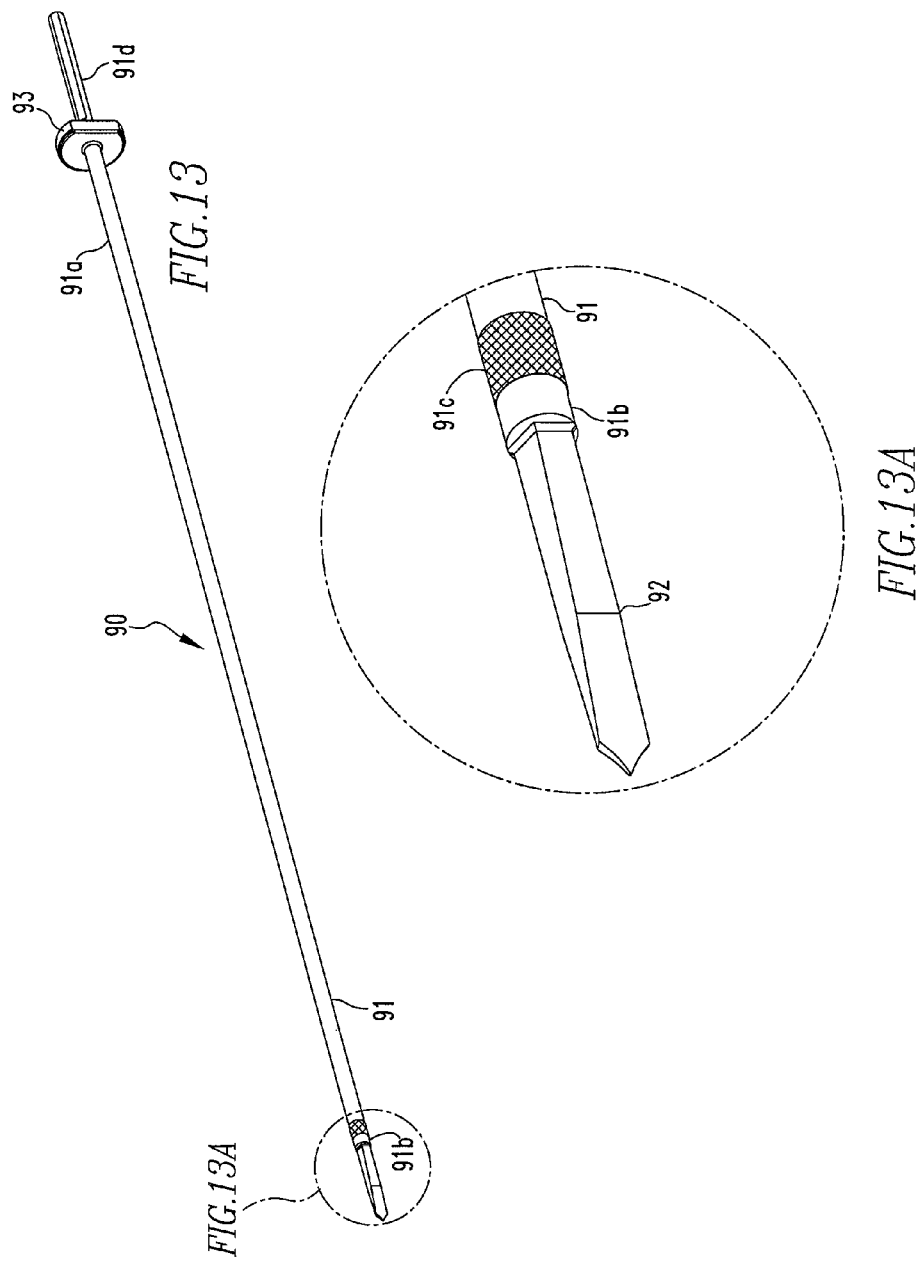

ANCHOR DELIVERY SYSTEM

CROSS-REFERENCE TO RELATED APPLICATIONS

This application is a divisional of U.S. application Ser. No. 14/274,977, filed on May 12, 2014, which is a divisional of U.S. application Ser. No. 11/839,721, filed Aug. 16, 2007, now U.S. Pat. No. 8,758,367, which is issued on Jun. 24, 2014, which claimed benefit of U.S. Provisional Application No. 60/824,573, filed Sep. 5, 2006, all applications are incorporated by reference herein in their entireties.

BACKGROUND OF THE INVENTION

Field of the Invention

The present disclosure relates to methods and devices for use in surgical procedures and, more specifically, to an arthroscopic method and apparatus for installing a suture anchor into bone.

Related Art

Medical devices and methods for attaching soft tissue to bone have been developed. Of particular interest, especially in sports medicine procedures, are suture anchors. A suture anchor is typically inserted into and fixed in a bore hole drilled into a bone at a surgical repair site. Sutures are typically coupled to the anchor and are used to secure the soft tissue to the bone in order to effect the repair. For many repair procedures, accuracy in the placement of suture anchors in bone is required to achieve consistently positive surgical outcomes, requiring substantial skill on the part of the surgeon.

Accurate placement of bore holes and suture anchors can be particularly challenging when repair is performed arthroscopically, as both access to and visibility of an arthroscopic surgical site may be more limited than is the case with open surgical procedures. For example, accurately drilling bore holes and placing suture anchors into these holes, at certain joint areas of the body, can be difficult for even a very experienced surgeon. This is due to the delivery devices not being able to reach a preferred anchor delivery point, not being able to achieve the preferred anchor trajectory, or both. In addition to these access and visualization problems, current devices used in the delivery of suture anchors cannot withstand the forces imposed by new techniques.

With the increasing popularity of arthroscopic repairs on the shoulder and hip, as well as repairs in other body joints including the ankle, knee, elbow, and foot, surgeons increasingly need to perform these procedures accurately and repeatably.

Accordingly, a need exists for devices and methods that provide for the accurate placement of suture anchors used in arthroscopic surgical procedures.

SUMMARY OF THE INVENTION

An aspect of the present disclosure relates to an anchor delivery system. The system includes a guide and an anchor delivery tool disposed within the guide. The tool includes a shaft and a handle coupled to the shaft. The handle includes a hub and a nose cone coupled to the hub. In an embodiment, the tool further includes a knob coupled to the hub and located between the handle and the nose cone. In another embodiment, the system further includes an anchor, such as a suture anchor, coupled to a distal portion of the shaft. In yet another embodiment, a shaft of the guide is bent relative to a longitudinal axis of the guide. In a further embodiment, the anchor delivery guide includes a high strength material.

In another aspect, the present disclosure relates to an anchor delivery tool. The tool includes a shaft and a handle coupled to the shaft. The handle includes a hub and a nose cone coupled to the hub. In an embodiment, the tool further includes a knob coupled to the hub and located between the handle and the nose cone. In an embodiment, the handle includes at least one suture retaining feature, such as a tab. In another embodiment, the handle includes multiple suture retaining features. In yet another embodiment, the handle includes a through passage extending a length of the handle. In a further embodiment, the knob is movable between a first position and a second position with respect to the nose cone. In yet a further embodiment, the knob is spring-loaded against the nose cone. In another embodiment, the knob includes laterally extending wings. In yet another embodiment, the nose cone includes a cavity wherein the cavity houses a distal portion of the knob when the knob is in a first position. In a further embodiment, the shaft includes an area of reduced diameter, wherein a length of the area is about 3 mm. In yet a further embodiment, the shaft includes at least two channels extending a length of the shaft. In another embodiment, the shaft includes a tip, the tip extending from a distal portion of the shaft.

In yet another aspect, the present disclosure relates to a method of repairing soft tissue. The method includes providing a guide; providing an anchor delivery tool, the tool including a shaft and a handle coupled to the shaft, the shaft including a suture anchor coupled to a distal end of the shaft, the handle including a hub and a nose cone coupled to the hub; introducing the guide into a body; advancing the tool through the guide; placing the anchor in bone; and securing the tissue to the bone with the suture.

In an embodiment, the method further includes a knob coupled to the hub and located between the handle and the nose cone. In an embodiment, the method includes introduction of the guide into the body occurring in a percutaneous manner via the use of an obturator, such as a cannulated obturator. In another embodiment, full advancement of the tool into the guide is obtained when a distal portion of the nose cone abuts a proximal portion of the guide. The distal portion of the nose cone and the proximal portion of the guide are flat. In yet another embodiment, full advancement of the tool into the guide is obtained when a laser mark at a distal portion of the tool is centered in an opening at a distal portion of the guide. In a further embodiment, a proximal portion of the anchor is located about 3 mm below a surface of the bone when a distal portion of the nose cone abuts a proximal portion of the guide. In yet a further embodiment, a proximal portion of the anchor is located about 3 mm below a surface of the bone when a laser mark at a distal portion of the tool is centered in an opening at a distal portion of the guide. In another embodiment, the tool is located at an angle of about 90 degrees relative to the bone upon placement of the anchor in the bone. In yet another embodiment, the tool is located at an angle of less than about 90 degrees relative to the bone upon placement of the anchor in the bone. In a further embodiment, the tool is located at an angle of more than about 90 degrees relative to the bone upon placement of the anchor in the bone.

Further areas of applicability of the present disclosure will become apparent from the detailed description provided hereinafter. It should be understood that the detailed description and specific examples, while indicating the preferred embodiment of the present disclosure, are intended for purposes of illustration only and are not intended to limit the scope of the present disclosure.

BRIEF DESCRIPTION OF THE DRAWINGS

The accompanying drawings, which are incorporated in and form a part of the specification, illustrate the embodiments of the present disclosure and together with the written description serve to explain the principles, characteristics, and features of the disclosure. In the drawings:

FIG. 1A shows an enlarged view of a distal portion of the guide of FIG. 1.

FIG. 3 shows an isometric view of a second alternative embodiment of the guide of FIG. 1.

FIG. 3A shows an enlarged view of a distal portion of the guide of FIG. 3.

FIG. 4 shows a side view of the guide of FIG. 3.

FIG. 5 shows an isometric view of a third alternative embodiment of the guide of FIG. 1.

FIG. 5A shows an enlarged view of a distal portion of the guide of FIG. 5.

FIG. 6 shows a side view of the guide of FIG. 5.

FIG. 7 shows an isometric view of the anchor delivery tool and anchor of the present disclosure.

FIG. 7A shows an enlarged view of a distal portion of the anchor delivery tool and anchor of FIG. 7.

FIG. 8 shows an isometric view of the anchor delivery system of the present disclosure.

FIG. 8A shows an enlarged view of a distal portion of the anchor delivery system of FIG. 8.

FIG. 9 shows a cross-sectional view of the anchor delivery system of the present disclosure.

FIG. 9A shows an enlarged view of the nose cone and the knob of the anchor delivery system of FIG. 9.

FIG. 10 shows an isometric view of an obturator of the present disclosure.

FIG. 10A shows an enlarged view of a distal portion of the obturator of FIG. 10.

FIG. 11 shows an isometric view of an alternative embodiment of the obturator of FIG. 10.

FIG. 11A shows an enlarged view of a distal portion of the obturator of FIG. 11.

FIG. 13 shows an isometric view of a drill bit of the present disclosure.

FIG. 13A shows an enlarged view of a distal portion of the drill bit of FIG. 13.

DETAILED DESCRIPTION OF THE EMBODIMENTS

The following description of the preferred embodiment(s) is merely exemplary in nature and is in no way intended to limit the disclosure, its application, or uses.

Figure 1:
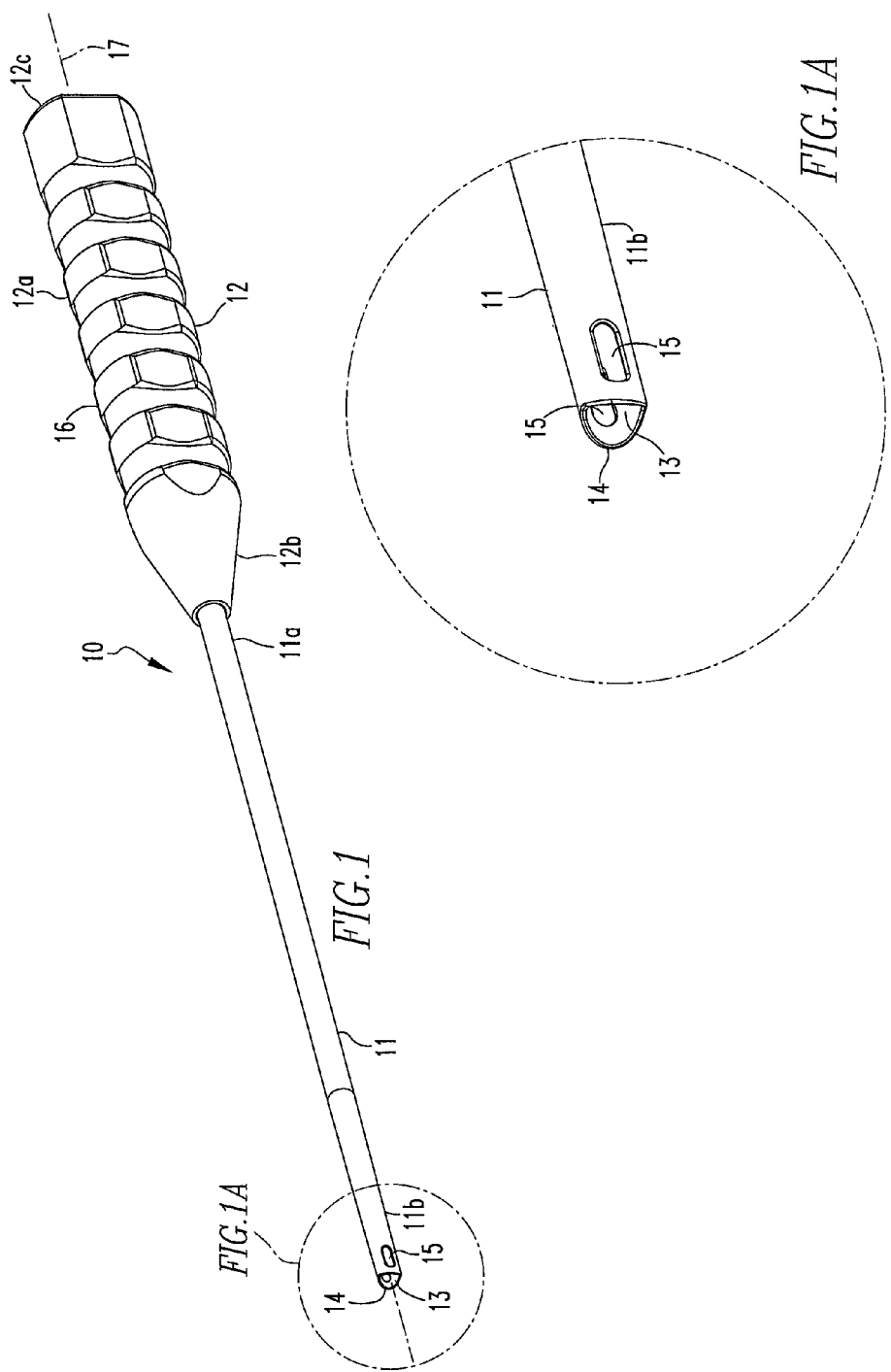
FIG. 1 shows an isometric view of the guide of the present disclosure.

FIG. 1 shows a guide 10 of the present disclosure. The guide 10 includes a shaft 11 coupled to a handle 12. A central passage 13 extends through the shaft 11 and the handle 12 for receiving a drill and an anchor delivery tool, as described in more detail below. The shaft 11 includes a proximal portion 11a and a distal portion 11b. The distal portion 11b, shown in FIG. 1A, includes a V-shaped tip 14 and an open side window 15. For the purposes of this disclosure, there are two open side windows 15 formed on opposite sides of the shaft 11. However, there may be more or less than two. In addition, the windows 15 are located as distal as possible as the space to view them arthroscopically is small in some joints, such as the hip. Although, the windows 15 may be located more or less distal. The proximal portion 11a is coupled to the handle 12 and partially extends a length of the handle 12. The handle 12 includes a body 12a, a tapered distal portion 12b, and a flat proximal portion 12c. Having a flat proximal portion 12c allows a surgeon to visualize the depth that a drill and anchor are advanced into bone, thereby substantially reducing the possibility of parallax and other depth control issues that may be found in other designs, as further described below. Similarly, having a tapered distal portion 12b allows a surgeon to impart deeper penetration of the guide 10 into a body, if needed, during surgery, as will be further described below. The distal 12b and proximal 12c portions may be of a shape other than tapered or flat. The body 12a includes circumferentially extending ribs 16 along a length of the body 12a for maintaining a grip on the handle 12 while imparting axial compression and bending into the guide 10 during surgery, as will be further described below. However, other means for maintaining a grip, known to one of ordinary skill in the art, may be used. The guide 10 also includes a longitudinal axis 17 along its length.

For the purposes of this disclosure, the guide 10 includes a high strength material, such as a high strength stainless steel material, in order to substantially reduce the possibility of plastic deformation of the guide 10 when it is subjected to various bending forces during surgery, as will be further described below. However, other high strength material known to one of ordinary skill in the art can be used.

Figure 2:
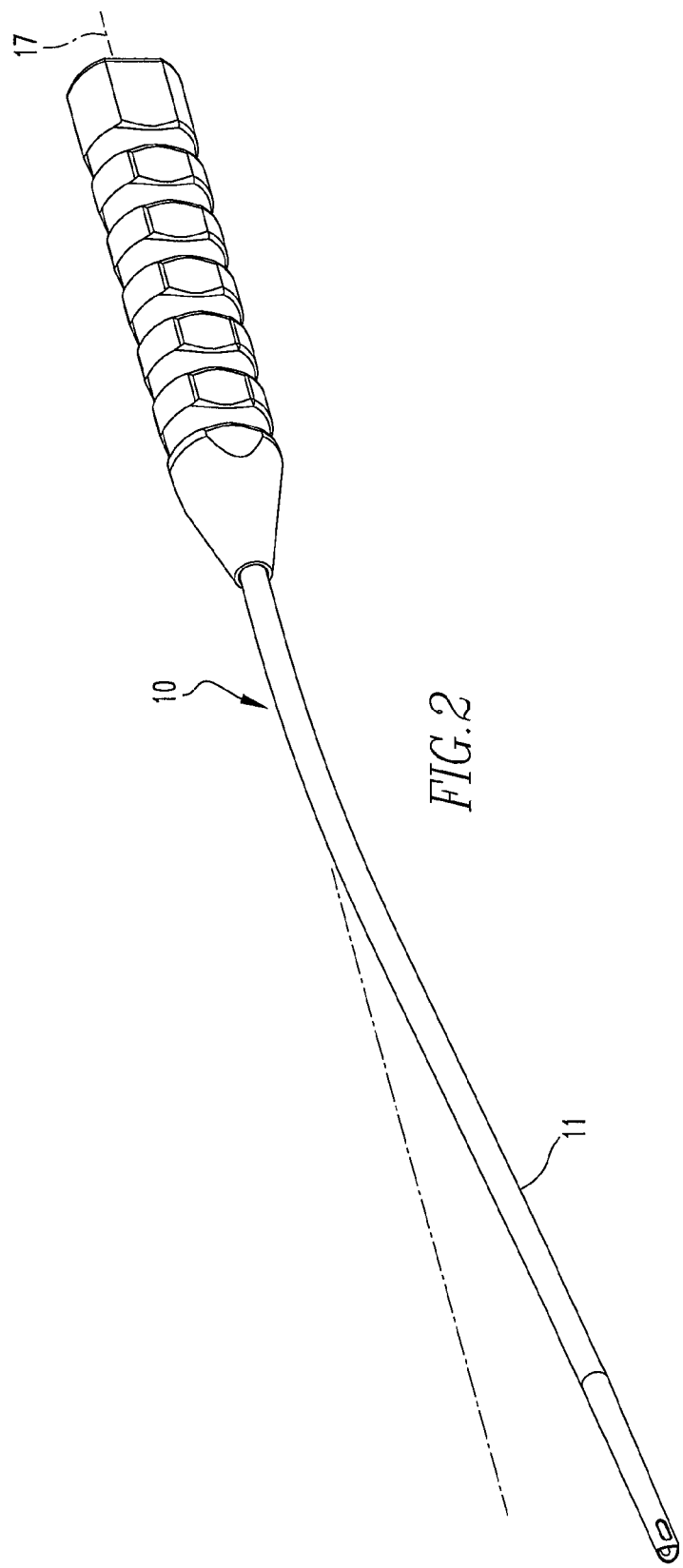
FIG. 2 shows an isometric view of a first alternative embodiment of the guide of FIG. 1.

FIG. 2 shows an alternative embodiment of the guide 10 of FIG. 1 wherein the shaft 11 of the guide 10 is bent or curved relative to the longitudinal axis 17 of the guide 10. The bend or curve is incorporated into the shaft 11 to direct the drill and an anchor on the anchor delivery tool around anatomy during surgery, especially anatomy that prevents a straight trajectory.

FIGS. 3 and 4 show an alternative embodiment of the guide 10 of FIG. 1. Specifically, the distal portion 21b of the guide 20, as more clearly shown in FIG. 3a, includes a forked tip 24 and an open side window 25. Similarly, FIGS. 5 and 6 show another alternative embodiment of the guide 10 of FIG. 1. Specifically, the distal portion 31b of the guide 30, as more clearly shown in FIG. 5A, includes a crown-shaped tip 34 and open side windows 35. Other shapes may be used for the tip of the distal portion of the shaft.

FIG. 7 shows the anchor delivery tool 40 and anchor 45 of the present disclosure and FIGS. 8 and 9 show the anchor delivery system 50 of the present disclosure. The tool 40 includes a shaft 41 and a handle 42 coupled to the shaft 41. The shaft 41 includes a proximal portion 41a and a distal portion 41b. The distal portion 41b, as more clearly shown in FIG. 8a, includes an area of reduced diameter 43 and a tip 44 that extends from the distal portion 41b. The area of reduced diameter 43 includes a length of about 3 mm and is used for depth stop and relief purposes, as will be further described below. As shown in FIG. 7A, a laser mark 41c is also located at the distal portion 41b of the anchor delivery tool 40 for depth control purposes, as will be further described below.

As also shown in FIG. 7A, a suture anchor 45 is coupled to the tip 44 of the tool 40. The anchor 45 includes an anchor body 45a having an anchoring portion 45b and a plug portion 45c. The anchoring portion 45b includes at least two slots 45d, extending a length of the anchoring portion 45b, and laterally extending barbs 45e. The plug portion 45c includes a passage 45f that extends through the plug portion 45c. A suture 46, having two free ends 46a, is disposed within the passage 45f such that both ends 46a are housed within the slots 45d of the anchoring portion 45b, as shown by the arrow 45h pointing to the slots 45d. The tip 44 interfaces with an opening (not shown) in a proximal portion 45g of the anchor 45. The anchor 45 is more fully explained in U.S. Provisional Patent Application 60/896,520, which is incorporated herein by reference in its entirety. The shaft 41 also includes two channels 47 that extend from the area of reduced diameter 43 to the proximal portion 41 a. For suture management purposes during surgery, the two free ends 46a of suture 46 extend along a length of both the anchor 45 and the shaft 41, are housed in the slots 45d and channels 47, and extend through a proximal portion 42e of the handle 42.

As more clearly shown in FIG. 9, the proximal portion 41a of the shaft 41 is coupled to the handle 42. The handle 42 includes a hub 42a, a nose cone 48 coupled to the hub 42a, and a knob 49 coupled to the hub 42a and located between the nose cone 48 and the handle 42. The handle 42 further includes two suture retaining features 42b, or tabs, for retaining suture 46 during surgery, as will be further described below, laterally extending ribs 42c for maintaining a grip on the handle 42 while imparting axial compression during surgery, and a through passage 42d. The nose cone 48 includes a flat distal portion 48a, a proximal portion 48b, and a cavity 48c. In addition, the nose cone 48 includes a slotted opening 48d for housing suture during surgery, as will be further described below, and a bore 48e. The bore 48e is sized such that the nose cone 48 tightly fits the hub 42a. The knob 49 includes a distal portion 49a that is housed within the cavity 48c when the distal portion 49a is in a first position, as shown in FIGS. 7-9 and as will be further described below, a proximal portion 49b, laterally extending wings 49c, and a bore 49h. The bore 49h is sized such that the knob 49 easily slides on the hub 42a. In addition, as shown more clearly in FIG. 9A, the knob 49 also includes a cavity 49d that houses a spring 49e for spring loading of the knob 49 against the nose cone 48 and for adjusting the knob 49 between a first position 49f, as described above, and a second position 49g, as more clearly shown in FIG. 9A.

As shown in FIG. 7, once the two free ends 46a of the suture 46 are extended through the handle 42, the ends 46a may be wound around the tabs 42b of the handle 42, as represented by the arrows 42b', and subsequently placed within the slotted opening 48d to be retained between the knob 49 and the nose cone 48 during delivery of the anchor 45 into bone, as will be further described below.

FIG. 10 shows an obturator 60 that may be used for percutaneous introduction of the guide 10 into the body. The obturator 60 includes a shaft 61 coupled to a handle 62. The shaft 61 includes a proximal portion 61a and a distal portion 61b. As shown more clearly in FIG. 10A, the distal portion 61b includes a conical, atraumatic tip 61c for easier passage of the obturator 60 through the body. Also shown in FIG. 10A is a through passage 61d that extends a length of the shaft 61 and is coaxial with a through passage 62a that extends a length of the handle 62. In use, the obturator 60 is inserted through the central passage 13 of the guide 10 and the combination is then passed over a previously implanted guide wire to be introduced into the body and delivered to the desired site for tissue repair. After delivery of the guide 10 into the body, the guide wire is removed. The obturator 60 allows for easier percutaneous introduction of the guide 10 to a desired site within the body by filling the inner diameter of the central passage 13 and substantially reducing the possibility of the tip 14 from becoming caught on tissue within the body.

Figure 12:
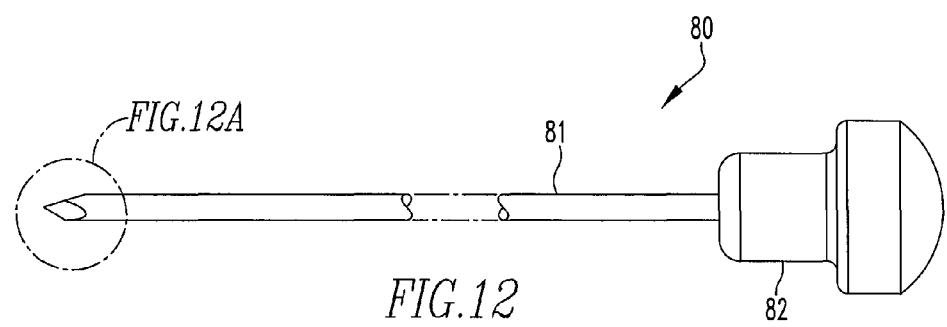
FIG. 12 shows a side view of an alternative embodiment of the obturator of FIG. 10.
Figure 12A:
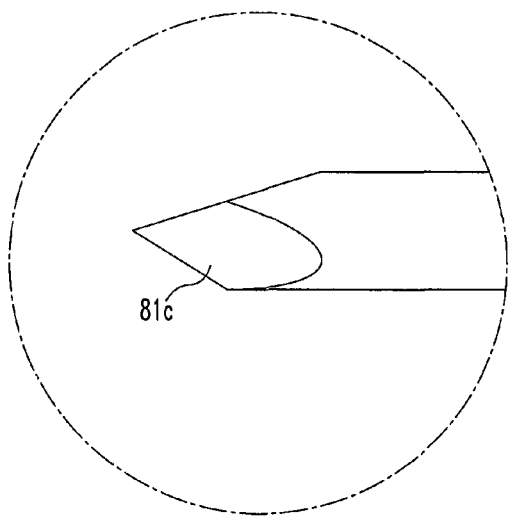
FIG. 12A shows an enlarged view of a distal portion of the obturator of FIG. 12.

FIGS. 11 and 12 show alternative embodiments of the obturator 60 of FIG. 10. Specifically, the obturators 70,80 do not include through passages extending the lengths of the shafts 71,81 and the handles 72,82. Similar to the tip 61c of the obturator 60 of FIG. 10, the tip 71c of the obturator 70 of FIG. 11 has a conical, atraumatic shape, as more clearly shown in FIG. 11A. However, the obturator 80 of FIG. 12 has a sharp, pointed tip 81c, as more clearly shown in FIG. 12A. Unlike the obturator 60 of FIG. 10, the obturators 70,80 of FIGS. 11 and 12 are not used for percutaneous introduction of the guide 10 into the body. Rather, obturators 70,80 are used for introduction of the guide 10 through the seal of a previously implanted cannula and subsequently into the body and to a desired site for tissue repair.

Once the obturator/guide combination reaches the desired site, the tip 14 of the guide 10 is placed against the bone to stabilize the guide 10, for subsequent drilling and anchor delivery, and the obturator 60 is then removed from the central passage 13 of the guide 10.

FIG. 13 shows a drill bit 90 that may be used for drilling of a hole into a bone. The drill bit 90 includes a shaft 91 having a proximal portion 91a and a distal portion 91b. As more clearly shown in FIG. 13A, a sharp, pointed tip 92 extends from the distal portion 91b of the shaft 91. In addition, a laser mark 91c is also located at the distal portion 91b of the drill bit 90 for depth control purposes, as will be further described below. The proximal portion 91a includes a depth stop 93 and an attachment area 91d for coupling of a drive unit (not shown) used to rotate the drill bit 90 and drill a hole into bone. After insertion of the guide 10 into the body and subsequent removal of the obturator 60 from the guide 10, the drill bit 90 is inserted into the central passage 13 of the guide 10 and a drive unit (not shown) is coupled to the attachment area 91d. The drive unit is then operated to rotate the drill bit 90 and drill a hole into the bone. The laser mark 91c and the depth stop 93 cooperate to control the depth of the hole such that the depth stop 93 abuts the flat proximal portion 12c of the guide handle 12 at the same time that the laser mark 91c becomes centered within the side windows 15 of the shaft 11. At this time, full advancement of the drill bit 90 into the guide 10 has occurred, drilling of the hole is finished, and the drill bit 90 is removed from the central passage 13 of the guide 10.

Figure 14:
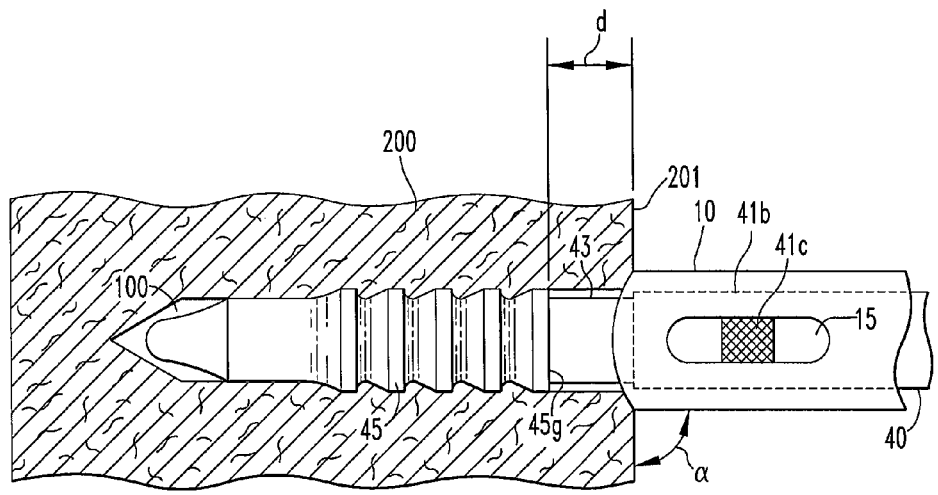
FIG. 14 shows a side view of anchor delivery into a bone by the anchor delivery system of FIG. 8.

Subsequent to removal of the drill bit 90 from the guide 10, the anchor delivery tool 40 is disposed within the central passage 13 of the guide 10, as shown in FIGS. 8 and 9, for delivery of the anchor 45 into the previously-drilled hole 100, as shown in FIG. 14. The anchor 45 is advanced into the hole 100 in an axially-oriented manner by tapping on a proximal portion 42e of the handle 42. Similar to the drilling procedure described above, full advancement of the tool 40 into the guide 10 is achieved when the flat distal portion 48a of the nose cone 48 abuts the flat proximal portion 12c of the guide handle 12. At this same time, the laser mark 41c is centered within the side windows 15 of the shaft 11. The distal portion 48a of the nose cone 48 and the proximal portion 12c of the guide handle 12 are both flat in order to substantially reduce the visualization problems, such as parallax, and the resultant interpretation that is currently required for determining drill and anchor bone depths.

Figure 15:
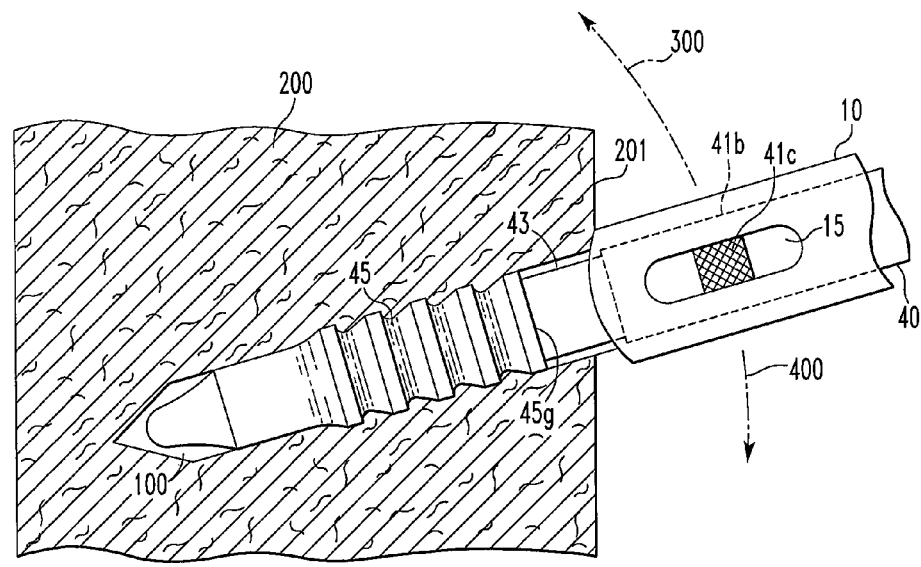
FIG. 15 shows a side view of an alternative anchor delivery into a bone by the anchor delivery system of FIG. 8.

When full advancement occurs, the proximal portion 45g of the anchor 45 is positioned a distance d of about 3 mm below a surface 201 of the bone 200. FIG. 14 shows the tool 40 located at an angle α, about 90°, relative to the surface 201 of the bone 200 upon placement of the anchor 45 into the bone 200. However, as also shown in FIG. 15, the tool 40 may be located at an angle of less or more than about 90 degrees relative to a surface 201 of the bone 200, as represented by arrows 300,400, upon placement of the anchor 45 in the bone 200, and still deliver the anchor into the bone such that the proximal portion 45g of the anchor 45 is positioned a distance of about 3 mm below a surface 201 of the bone 200. As described above, the distal portion 41b of the shaft 41 includes an area of reduced diameter 43 having a length of about 3 mm. The area 43 is included on the distal portion 41b to substantially reduce the possibility of the distal portion 41b from getting stuck in the hole 100 of the bone 200 during delivery of the anchor 45 into the hole 100. However, the area 43 can also serve as a depth stop, especially when the nose cone 48 is not used, to ensure that the proximal portion 45g of the anchor 45 is positioned a distance of about 3 mm below a surface 201 of the bone 200.

Once the anchor 45 has been delivered into the bone 200, the two free ends 46a of suture 46 are released from between the knob 49 and the nose cone 48 by moving the knob 49 toward the handle 42 and into a second position 49g, as shown in FIG. 9. The anchor delivery system 50 is subsequently removed from the body, thereby leaving the anchor 45 and suture 46 in the bone. The suture 46 is then used to secure a tissue to the bone 200.

For the purposes of this disclosure, the anchor 45 includes a bioabsorbable polymer material. However, the anchor 45 may be made from a biocompatible metal material, such as titanium. In addition, the shaft 41 and the through passage 42d are sized such that the shaft 41 is press-fit into the through passage 42d. Those of ordinary skill in the art would understand that the shaft 41 and the handle 42 may be assembled in other ways. As examples, the shaft 41 and the handle 42 may be assembled by heat staking, ultrasonic staking, spin welding, insert molding, or other methods known to one of ordinary skill in the art. The shaft 41 includes stainless steel, but may be made from another biocompatible material known to one of ordinary skill in the art. Also for the purposes of this disclosure, the handle 41 may include less than or more than two suture retaining features 42b. In addition, the features 42b are integral with the handle, but may be a separate component, and may be of any number of geometric shapes.

The nose cone 48 is insert molded to the shaft 41. In this case, the hub 42a is placed in a mold and the nose cone 48 is molded around the hub 42a. Those of ordinary skill in the art would understand that the nose cone 48 may be coupled to the hub 42a by heat staking, ultrasonic staking, spin welding, or by any other method known to one of ordinary skill in the art. In addition, the nose cone 48, knob 49, suture retaining features 42b, and handle 42 include a non-metal material, but may include a metal material or other biocompatible material known to one of ordinary skill in the art. Also, the laser marks 41c,91c may be any other type of visible mark and may be of a variety of widths.

The shafts 61,71,81 and handles 62,72,82 of the obturators 60,70,80 are made from stainless steel and plastic, respectively. However, either one could be made from any other biocompatible material known to one of ordinary skill in the art. The shafts 61,71,81 are press-fit to the obturators 60,70,80, but could be coupled to the obturators 60,70,80 by any other method known to one of ordinary skill in the art. The drill bit 90 is made from stainless steel, but it could be made from any other biocompatible material known to one of ordinary skill in the art.

As various modifications could be made to the exemplary embodiments, as described above with reference to the corresponding illustrations, without departing from the scope of the present disclosure, it is intended that all matter contained in the foregoing description and shown in the accompanying drawings shall be interpreted as illustrative rather than limiting. Thus, the breadth and scope of the present disclosure should not be limited by any of the above-described exemplary embodiments, but should be defined only in accordance with the following claims appended hereto and their equivalents.

What is claimed is:

1. An anchor delivery tool comprising:
   a shaft and a handle coupled to the shaft, the handle including a hub, a nose cone and a knob coupled to the hub, wherein the knob is configured to slide relative to the nose cone so as to selectively retain and release a length of suture disposed along an outer surface of the knob, and wherein the knob is spring loaded against the nose cone.

2. The anchor delivery tool of claim 1 wherein the knob is slidingly coupled to the hub and proximally located relative to the nose cone.

3. The anchor delivery tool of claim 1 wherein the handle includes at least one suture retaining feature.

4. The anchor delivery tool of claim 3 wherein the suture retaining feature comprises a tab disposed on an outer surface of the handle.

5. The anchor delivery tool of claim 3 wherein the handle includes multiple axially spaced suture retaining features.

6. The anchor delivery tool of claim 1 wherein the handle includes a through passage extending a length of the handle having an opening on an outer surface of the handle at a handle proximal end portion.

7. The anchor delivery tool of claim 1 wherein the knob and an outer surface of the hub define an annular cavity comprising a spring, configured to bias the knob into a cavity of the nose cone.

8. The anchor delivery tool of claim 1 wherein the knob includes laterally extending wings.

9. The anchor delivery tool of claim 1 wherein the nose cone includes a cavity, the cavity housing a distal portion of the knob.

10. The anchor delivery tool of claim 1 wherein the shaft includes an area of reduced diameter.

11. The anchor delivery tool of claim 10 wherein the area of reduced diameter includes a length of about 3 mm.

12. The anchor delivery tool of claim 1 wherein the shaft includes at least two channels extending a length of the shaft.

13. The anchor delivery tool of claim 1 wherein the shaft includes a tip, the tip extending from a distal portion of the shaft.

14. The anchor delivery tool of claim 1 wherein the knob is configured to slide relative to the nose cone, between a suture retaining position wherein a knob distal end is disposed within an inner cavity of the nose cone and abuts an inner cavity surface of the nose cone so as to secure the length of suture disposed therebetween and a suture releasing position wherein the knob distal end is spaced away from an inner cavity surface.

15. An anchor delivery tool comprising:
a shaft and a handle coupled to the shaft, the handle having a hub portion defining a distal portion of the handle, and wherein a nose cone and a knob are disposed around the hub portion, the knob configured to slide axially along the hub portion so as so define a first position wherein a knob distal end is disposed within an inner cavity of the nose cone and abuts an inner cavity surface of the nose cone so as to secure a length of suture therebetween and a second position wherein the knob distal end is spaced away from the inner cavity surface to release the length of suture.

16. The anchor delivery tool of claim 15 wherein the handle includes at least one suture retaining feature disposed on an outer surface of the handle.

17. The anchor delivery tool of claim 16 wherein the handle includes a through passage extending a length of the handle having an opening on an outer surface of a handle proximal end portion, the opening and passage to provide a portion of a suture path from an anchor associated with the anchor delivery tool, the suture path extending along the passage, through the opening and around the at least one suture retaining feature.

18. The anchor delivery tool of claim 15 wherein the knob and hub define an annular cavity, housing a spring disposed around the hub, configured to bias the knob in the first position.

19. The anchor delivery tool of claim 15 wherein the nose cone cavity defines an annular opening at the nose cone proximal end.

* * * * *